(12) United States Patent
Keränen (10) Patent No.: US 9,056,009 B2
(45) Date of Patent: Jun. 16, 2015

(54) DEVICE AND METHOD FOR IMPROVING FUNCTION OF HEART VALVE

(75) Inventor: Olli Keränen, Bjärred (SE)

(73) Assignee: Medtentia International Ltd. Oy, Helsinki (FI)

( * ) Notice: Subject to any disclaimer, the term of this patent is extended or adjusted under 35 U.S.C. 154(b) by 52 days.

(21) Appl. No.: 13/525,093

(22) Filed: Jun. 15, 2012

(65) Prior Publication Data

US 2012/0316640 A1 Dec. 13, 2012

Related U.S. Application Data

(62) Division of application No. 12/514,795, filed as application No. PCT/EP2007/062225 on Nov. 12, 2007, now Pat. No. 8,663,322.

(60) Provisional application No. 60/876,123, filed on Dec. 21, 2006.

(30) Foreign Application Priority Data

Nov. 13, 2006 (SE) ...................................... 0602421

(51) Int. Cl.
*A61F 2/24* (2006.01)

(52) U.S. Cl.
CPC ............. *A61F 2/2445* (2013.01); *A61F 2/2448* (2013.01); *A61F 2230/0091* (2013.01)

(58) Field of Classification Search
CPC ... A61F 2/2433; A61F 2/2412; A61F 2/2427; A61F 2/2442; A61F 2/2445; A61F 2/2475; A61F 2/2478

USPC ........................ 623/2.36, 1.24, 2.1, 2.17, 2.37
See application file for complete search history.

(56) References Cited

U.S. PATENT DOCUMENTS

| | | | |
|---|---|---|---|
| 4,042,979 A | 8/1977 | Angell | |
| 6,368,348 B1 | 4/2002 | Gabbay | |
| 6,419,696 B1 | 7/2002 | Ortiz et al. | |
| 6,585,767 B1 | 7/2003 | Holley et al. | |
| 6,790,229 B1 | 9/2004 | Berreklouw | |
| 7,445,632 B2 * | 11/2008 | McGuckin et al. | 623/2.37 |
| 7,803,184 B2 * | 9/2010 | McGuckin et al. | 623/2.1 |
| 7,942,927 B2 * | 5/2011 | Kaye et al. | 623/2.11 |
| 8,167,935 B2 * | 5/2012 | McGuckin et al. | 623/2.37 |

(Continued)

FOREIGN PATENT DOCUMENTS

| | | | | |
|---|---|---|---|---|
| WO | WO 03028558 A2 * | 4/2003 | | A61F 17/00 |
| WO | WO 2006/054930 A1 | 5/2006 | | |
| WO | WO 2006/091163 A1 | 8/2006 | | |

OTHER PUBLICATIONS

United States Patent and Trademark Office, Office Action mailed Jan. 9, 2012 in U.S. Appl. No. 12/514,795, 11 pages.

(Continued)

*Primary Examiner* — Thomas J Sweet
*Assistant Examiner* — Seema Mathew
(74) *Attorney, Agent, or Firm* — Inskeep IP Group, Inc.

(57) ABSTRACT

A device for improving the function of a heart valve comprises a first loop-shaped support, which is configured to abut a first side of the heart valve, and a first flange unit being connected to said first loop-shaped support. The flange unit is configured to be arranged against said annulus when said first loop-shaped support is abutting said heart valve.

15 Claims, 10 Drawing Sheets

(56) References Cited

U.S. PATENT DOCUMENTS

| | | | |
|---|---|---|---|
| 8,657,872 B2* | 2/2014 | Seguin | 623/2.38 |
| 2002/0173841 A1 | 11/2002 | Ortiz et al. | |
| 2003/0045929 A1 | 3/2003 | McCarthy et al. | |
| 2003/0199975 A1 | 10/2003 | Gabbay | |
| 2004/0127981 A1* | 7/2004 | Rahdert et al. | 623/2.36 |
| 2004/0138745 A1* | 7/2004 | Macoviak et al. | 623/2.36 |
| 2004/0260393 A1* | 12/2004 | Rahdert et al. | 623/2.36 |
| 2005/0010287 A1* | 1/2005 | Macoviak et al. | 623/2.36 |
| 2005/0038508 A1* | 2/2005 | Gabbay | 623/2.36 |
| 2005/0137689 A1* | 6/2005 | Salahieh et al. | 623/2.11 |
| 2005/0256567 A1* | 11/2005 | Lim et al. | 623/2.36 |
| 2006/0100697 A1* | 5/2006 | Casanova | 623/2.11 |
| 2006/0195183 A1* | 8/2006 | Navia et al. | 623/2.18 |
| 2006/0206203 A1* | 9/2006 | Yang et al. | 623/2.37 |
| 2009/0054974 A1* | 2/2009 | McGuckin et al. | 623/2.1 |
| 2009/0276038 A1* | 11/2009 | Tremulis et al. | 623/2.11 |
| 2009/0299471 A1* | 12/2009 | Keranen | 623/2.37 |
| 2010/0280606 A1* | 11/2010 | Naor | 623/2.18 |
| 2011/0098802 A1* | 4/2011 | Braido et al. | 623/1.26 |
| 2011/0118828 A1* | 5/2011 | Thompson | 623/2.2 |
| 2011/0137397 A1* | 6/2011 | Chau et al. | 623/1.11 |
| 2011/0137410 A1* | 6/2011 | Hacohen | 623/2.37 |
| 2012/0059458 A1* | 3/2012 | Buchbinder et al. | 623/2.36 |
| 2012/0178360 A1* | 7/2012 | Park et al. | 455/7 |
| 2012/0179247 A1* | 7/2012 | Navia | 623/2.37 |
| 2012/0323317 A1* | 12/2012 | Karapetian et al. | 623/2.37 |
| 2013/0006352 A1* | 1/2013 | Yaron | 623/2.37 |
| 2013/0103142 A1* | 4/2013 | Subramanian et al. | 623/2.36 |
| 2013/0190861 A1* | 7/2013 | Chau et al. | 623/2.18 |
| 2013/0253643 A1* | 9/2013 | Rolando et al. | 623/2.37 |
| 2014/0005778 A1* | 1/2014 | Buchbinder et al. | 623/2.18 |
| 2014/0025164 A1* | 1/2014 | Montorfano et al. | 623/2.37 |
| 2014/0046434 A1* | 2/2014 | Rolando et al. | 623/2.11 |
| 2014/0088696 A1* | 3/2014 | Figulla et al. | 623/2.17 |
| 2014/0155997 A1* | 6/2014 | Braido | 623/2.37 |
| 2014/0303719 A1* | 10/2014 | Cox et al. | 623/2.11 |
| 2014/0324163 A1* | 10/2014 | Keranen et al. | 623/2.36 |
| 2014/0350670 A1* | 11/2014 | Keranen | 623/2.36 |
| 2014/0364945 A1* | 12/2014 | Longoria et al. | 623/2.36 |

OTHER PUBLICATIONS

WIPO, European International Preliminary Examining Authority, International Preliminary Report on Patentability mailed Nov. 24, 2008 in International Patent Application No. PCT/EP2007/062225, 7 pages.

WIPO, European International Search Authority, International Search Report and Written Opinion mailed Feb. 29, 2008 in International Patent Application No. PCT/EP2007/062225, 11 pages.

* cited by examiner

DEVICE AND METHOD FOR IMPROVING FUNCTION OF HEART VALVE

RELATED APPLICATIONS

This application is a divisional of U.S. patent application Ser. No. 12/514,795 filed Jan. 19, 2010 entitled Device And Method For Improving Function Of Heart Valve, which claims priority to International Patent Application No. PCT/EP2007/062225, International Filing Date 12 Nov. 2007, entitled Device And Method For Improving Function Of Heart Valve, and to Swedish Provisional Application No. 0602421-0 filed Nov. 13, 2006, and U.S. Provisional Application Ser. No. 60/876,123 filed Dec. 21, 2006, all of which are hereby incorporated herein by reference.

FIELD OF THE INVENTION

The present invention pertains in general to the field of repair of heart valves having various malformations and dysfunctions. More specifically, the invention relates to heart valve repair techniques and procedures involving annuloplasty devices.

BACKGROUND OF THE INVENTION

Diseased mitral and tricuspid valves frequently need replacement or repair. The mitral and tricuspid valve leaflets or supporting chordae may degenerate and weaken or the annulus may dilate leading to valve leak, i.e. an insufficiency of valve function. The leaflets and chords may become calcified and thickened rendering them stenotic, which implies obstructing a forward flow through the valve. Finally, the valve relies on insertion of the chordae inside the ventricle. If the ventricle changes in shape, the valve support may become non-functional and the valve may leak.

Mitral and tricuspid valve replacement and repair are traditionally performed with a suture technique.

During valve replacement, sutures are spaced around the annulus, i.e. the point where the valve leaflet attaches to the heart, and then the sutures are attached to a prosthetic valve. The prosthetic valve is lowered into position and when the sutures are tied, the prosthetic valve is fastened to the annulus. The surgeon may remove all or part of the valve leaflets before inserting the prosthetic valve.

In valve repair, a diseased valve is left in situ and surgical procedures are performed to restore its function. Frequently an annuloplasty ring is used to reduce the size of the annulus. The annuloplasty ring serves to reduce the diameter of the annulus and allows the leaflets to oppose each other normally, thus restoring valve function. Sutures are used to attach the prosthetic annuloplasty ring to the annulus and to assist in placating the annulus.

In general, the annuloplasty rings and replacement valves must be sutured to the valve annulus and this is time consuming and tedious. Moreover, if the annuloplasty ring is severely malpositioned, then the stitches must be removed by the surgeon, and the ring repositioned relative to the valve annulus during restitching. In other cases, a less than optimum annuloplasty may be tolerated by the surgeon rather than lengthening the time of the surgery to restitch the ring.

During heart surgery, a premium is placed on reducing the amount of time used to replace and repair valves as the heart is frequently arrested and without perfusion. In e.g. U.S. Pat. No. 6,368,348, an annuloplasty prosthesis is disclosed for supporting an annulus of a heart valve. The prosthesis is devised to be stitched to the annulus of the heart thus remodeling the same. It would therefore be very useful to have an improved method, procedure, and/or device providing an efficient attachment of a prosthesis into the mitral or tricuspid valve position.

For instance in US 2002/0173841 and in U.S. Pat. No. 6,419,696, which are assigned to the same applicant as the present application, an annuloplasty device is disclosed. The annuloplasty device comprises a first and a second support ring, which are connected to each other to form a coiled configuration. The first and second support rings are arranged to abut opposite sides of a valve annulus to trap valve tissue between them. This annuloplasty device may be easily applied to the valve by rotating the device into position on opposite sides of the valve annulus. To ensure a proper and lasting fixation to the valve annulus such device can be fixated by barbs, retaining members, interlocking portions, fasteners or locking elements, all being integrated in the device. Fixation can also be made by means of suturing.

In WO 2006/091163, which are assigned to the same applicant as the present application, a device for improving the function of a heart valve is disclosed that comprises a first loop-shaped support, which is configured to abut a first side of the heart valve, and a second loop-shaped support, which is configured to abut a second side of the heart valve opposite to said first side, whereby a portion of the valve tissue is trapped between the first and second supports. An outer boundary of the second support is greater than an outer boundary of the first support. An annuloplasty instrument for implantation of the above mentioned device is disclosed in WO 2006/054930 by the same applicant as the present application. Thus deployment of the device in WO 2006/091163 is facilitated. These two above mentioned comprise a kit to be used together for the treatment of heart valve deficiencies. Paravalvular leakage is not addressed in these disclosures.

In U.S. Pat. No. 4,042,979 an adjustable valvuloplasty ring is disclosed that comprises a C-shaped frame that is sized and shaped to extend about the circumference of the left atrioventricular orifice along the base of the anterior cusp of the mitral valve; an expandable sleeve connected to the frame that together therewith forms a closed annulus, the sleeve being adapted to extend about the remainder of the circumference of the orifice; and a drawstring running through the sleeve by which the sleeve may be contracted to constrict and remodel the orifice and secured in place to maintain such constriction.

However, the prosthetic devices disclosed in the above mentioned documents might be further improved for a more convenient, faster positionable, and/or even more reliable device and method of valve repair and valve replacement. It is a specific object of the invention to provide a device, which allows for an easy and durable fixation to the valve annulus.

Furthermore, an improvement that is desired to be provided by improved devices and methods comprises allowing a prevention or minimization of backflow of blood, e.g. passing by or underneath the prosthetic devices of the prior art.

Hence, an improved annuloplasty device and medical procedure would be advantageous and in particular allowing for increased flexibility, cost-effectiveness, convenience and speed of positioning, increased reliability and/or patient safety would be advantageous.

OBJECTS AND SUMMARY OF THE INVENTION

An object of the invention is to provide an improved medical device and method of valve repair and valve replacement.

Another object of the invention may be to provide an annuloplasty device, which allows for an easy and durable fixation to the valve annulus.

Accordingly, embodiments of the present invention preferably seek to mitigate, alleviate or eliminate one or more deficiencies, disadvantages or issues in the art, such as the above-identified, singly or in any combination by providing a medical device and a method according to the appended patent claims.

According to a first aspect of the invention, there is provided a medical device for improving the function of a heart valve comprised of valve tissue including an annulus and a plurality of leaflets, the device comprising: a first loop-shaped support, which is configured to abut a first side of the heart valve, and a first flange unit (or flange element or flange means) being connected to said first loop-shaped support, and which is configured to be arranged against said annulus when said first loop-shaped support is abutting said heart valve.

This device may be used to perform annuloplasty, that is to reshape the valve annulus, in order to improve the function of the valve. The flange unit provides a well defined surface to be used when fixating the device against the annulus no matter if the device in use is positioned abutting the atrial or the ventricle side of annulus.

This implies that the device may easily be fixated to the annulus in a speedy manner. This is of importance since during heart surgery, a premium is placed on reducing the amount of time used to replace and repair valves as the heart is frequently arrested and without perfusion.

Also, the flange unit may provide for a sealing surface against said annulus allowing prevention of backflow of blood from the ventricle side to the atrial side.

Further, the provision of a flange unit implies that a smooth transition section may be formed between the outer periphery of the device and annulus.

Further, a well defined surface for attachment of fixating means such as sutures or clips may be provided. A smooth transition section as well as a well defined attachment surface are two parameters of importance for a smooth formation and growth of endothelia.

In addition, the flange unit may be used for carrying or fixation of a prosthetic valve.

The device may further comprise a second loop-shaped support, which is configured to abut a second side of the heart valve opposite to said first side, whereby a portion of the valve tissue is trapped between the first and second supports. The trapping of valve tissue between the first and second loop-shaped supports implies that the desired shape of the valve, both natural or prosthetic, may be fixated. Further, the trapping implies that the device may temporarily be kept in correct position while fixating the device permanently to an annulus by means of e.g. sutures or clips.

The first loop-shaped support may be formed continuously with the second loop-shaped support to form a substantially coil-shaped body. This implies that the device and its coil-shape may be applied at a commissure between the leaflets of the heart valve and be rotated approximately 360° such that one loop-shaped support is inserted through the commissure to extend along one side of the valve and the other loop-shaped support is arranged along the opposite side of the valve. Thus, valve tissue will be trapped between the supports to fixate a desired shape of the valve. Depending on the extension of the flange means, the latter may provide an attachment surface on one of or on both sides of the annulus for fixation of the device.

The first flange unit may extend from the first loop-shaped support to the second loop-shaped support, whereby the flange unit may be configured to be arranged against the annulus on opposite sides of the valve tissue being trapped between the first and second supports. This implies that the flange unit may form a flange surface on both sides of the annulus or heart valve, which surface may provide for fixation, not only of the device but also of a prosthetic valve. Further, the flange unit may form a sealing surface that, depending on the position of the device, allows reduction or prevention of possible backflow of blood from the ventricle side to the atrial side.

The second loop-shaped support may comprise a second flange unit being connected thereto, which flange unit may be configured to be arranged against the annulus on a side thereof being opposite the first loop-shaped support when the second loop-shaped support is abutting the heart valve. This allows prevention of paravalvular leakage.

At least one of the first and second flange unit may be adapted to form a connection of at least one of the loop-shaped supports and a prosthetic valve against the annulus. This implies a rapid fixation, which is of importance since during heart surgery a premium is placed on reducing the time required.

At least one of the first and second flange unit may have an intermittent or continuous extension along the periphery of its corresponding loop-shaped support. By way of example, in case of an intermittent extension the flange unit may be formed by two local sections diametrically opposing each other, whereby the two sections, when the device is positioned in the heart valve, are abutting the commissures forming a sealing surface thereto.

At least one of the first and second flange units may be made of a fabric material. The fabric material may be a woven material. A fabric has the advantage that it presents a rough surface enhancing ingrowth or anchoring of endothelia. Further, a fabric is easily penetrated by sutures or clips. Also, a fabric allows the flange unit to be easily conformed to the annulus.

The fabric material may be impregnated with or integrate a pharmaceutical agent further improving embodiments of the devices and method. The pharmaceutical agent may for instance be an anti inflammatory, stenos preventing, or endotheliazation promoting agent.

Further, at least one of the first and second flange unit may comprise a reinforcing element. The reinforcing element provides an indication and definition of an area in which clips or sutures are to be put when fixating the medical device to the annulus. Further, the reinforcing element contributes to reducing the risk of pockets being formed along the circumferential surface. Also, the element prevents unthreading of the fabric in the flange.

At least one of the first and second flange unit may protrude or extend out from and form an angle $\alpha$ (see e.g. FIG. 5) of approximately 30-60°, such as e.g. approximately 40-50° below a diametric plane formed by one of the loop-shaped supports. By the flange unit initially extending below the diametric plane, the visibility during insertion is enhanced. In some embodiments, during insertion, the flange unit due to inherent flexibility may be fold, e.g. upwards in FIG. 5, even fold back over its point of fixation relative the diametric plane, or above the diametric plane with an outer edge of the flange unit. The point of fixation of at least one of the flange unit may be fixed in relation to the diametric plane, radially outward from at least one of the loop-shaped supports.

The flange unit may protrude with other angles, even in a fold back, i.e. more than 90°. This may be during or prior to a time of use or implantation thereof. The angle may be variable over time, e.g. to the herein described shape memory effect of some embodiments of the flange unit.

The flange unit may in some embodiments be arranged to change shape during insertion, e.g. by a resilient arrangement thereof. The flange unit may also be made of a shape memory material that returns to a pre-defined shape of form during insertion of the medical device, e.g. by a temperature triggered effect as known in the art of shape memory materials.

At least one of the first and second flange unit extends radially inwards or outwards from its corresponding loop-shaped support. A radially inward extension provides a support for the valve leaflets, whereas a radially outward extension provides a support against the annulus. The first side of the heart valve is the atrial side and the second side is the ventricle side.

According to a second aspect of the invention there is provided a method for repairing a heart valve comprised of valve tissue including an annulus and a plurality of leaflets for allowing and preventing blood flow, the method comprising: inserting a device comprising at least one loop-shaped support and at least one flange unit being connected to the loop-shaped support to a heart valve, positioning the loop-shaped support such that it abuts a first side of the heart valve, positioning the flange unit such that it abuts the annulus, and fixating the device by attaching the flange unit to the annulus.

The advantages provided by a device having a flange unit have previously been discussed above. The inventive method for repairing a heart valve uses a corresponding device, whereby at least the same benefits are achieved.

The flange unit may be attached to the annulus by using sutures or clips, which allows for a quick and easy fixation using well established means. Alternatively, or in addition, barb elements or tissue adhesives may be used for the attachment to the annulus.

The provision of a flange unit implies that a smooth transition section may be formed between the outer periphery of the device and annulus. Further, the flange unit presents a well defined and easy detectable surface for attachment of the clips or sutures. A smooth transition section as well as a well defined attachment surface allows for a smooth formation and growth of endothelia. Endothelia formation may further be improved by an endotheliazation agent.

The flange unit may be conformed to the annulus before fixating the device. By conforming the flange unit, the transition section may be additionally smoothened, further enhancing growth of endothelia.

The device may be inserted to the heart valve by using a catheter, whereupon the catheter is withdrawn leaving the device.

In the method the first side of the heart valve may be the atrial side.

Further, in another aspect, the invention provides a kit comprising a device for improving the function of a heart valve comprised of valve tissue including an annulus and a plurality of leaflets, the device comprising: a first loop-shaped support, which is configured to abut a first side of the heart valve, and a first flange unit being connected to the first loop-shaped support, and which is configured to be arranged against the annulus when the first loop-shaped support is abutting the heart valve, and an artificial valve.

This device may be used in a medical procedure to perform annuloplasty, that is to reshape the valve annulus, in order to improve the function of the valve. The flange unit provides a well defined surface to be used when fixating the device against the annulus. This implies that the device may be fixated to the annulus very easily and in a speedy manner. The latter is of importance since during heart surgery, a premium is placed on reducing the amount of time used to replace and repair valves as the heart is frequently arrested and without perfusion. Also, the flange unit provides a sealing surface against the annulus allowing prevention of backflow of blood from the ventricle side to the atrial side. By the device carrying an artificial prosthetic valve, the steps and time involved when performing the surgery may be reduced. Further, the positioning of such prosthetic valve in relation to the annulus is facilitated.

The device may further comprise a second loop-shaped support, which is configured to abut a second side of the heart valve opposite to the first side, whereby a portion of the valve tissue is trapped between the first and second supports. The trapping of valve tissue between the first and second loop-shaped supports implies that the desired shape of the valve may be fixated. Further, the trapping implies that the device may temporarily be kept in correct position while substantially fixating the device permanently to an annulus by means of e.g. sutures or clips.

The first loop-shaped support may be continuous with the second loop-shaped support to form a coil-shaped body. This implies that the device and its coil-shape may be applied at a commissure between the leaflets of the heart valve and be rotated 360° such that one loop-shaped support is inserted through the commissure to extend along one side of the valve and the other loop-shaped support being arranged along the opposite side of the valve. Thus, valve tissue will be trapped between the supports to fixate a desired shape of the valve. Depending on the extension of the flange means, the latter may provide an attachment surface on one of or on both sides of annulus for fixation of the device.

The first flange unit may extend from the first loop-shaped support to the second loop-shaped support, whereby the flange unit may be configured to be arranged against the annulus on opposite sides of the valve tissue being trapped between the first and second supports. This implies that the flange unit may form a surface on both sides of the heart valve, which surface may be used for fixation, not only of the device but also of a prosthetic valve. Further, the flange unit may form a sealing surface that, depending on the position of the device, allows prevention of possible backflow of blood from the ventricle side to the atrial side.

The second loop-shaped support may comprise a second flange unit being connected thereto, which flange unit may be configured to be arranged against the annulus on a side thereof being opposite the first loop-shaped support when the second loop-shaped support is abutting the heart valve. This allows prevention of paravalvular leakage.

At least one of the first and second flange unit may have an intermittent or continuous extension along the periphery of its corresponding loop-shaped support. By way of example, in case of an intermittent extension the flange unit may be formed by two local sections diametrically opposing each other, whereby the two sections, when the device is positioned in the heart valve, are abutting the commissures forming a sealing surface thereto.

At least one of the first and second flange unit may be made of a fabric material. A fabric has the advantage that it presents a rough surface enhancing growth of endothelia. Further, a fabric is easily penetrated by sutures or clips. Also, a fabric allows the flange unit to be easily conformed to the annulus.

Further, at least one of the first and second flange unit may comprise a reinforcing element. The element provides an indication and definition of the area in which clips or sutures are to be put when fixating the device to the annulus. Further, the element reduces the risk of pockets being formed along the circumferential surface. Also, the element prevents unthreading of the fabric in the flange.

At least one of the first and second flange unit may extend out from and form an angle of 30-60°, such as 40-50° below a diametric plane formed by one of the loop-shaped supports. By the flange unit initially extending below the diametric plane, the visibility during insertion is enhanced.

At least one of the first and second flange unit may extend radially inwards or outwards from its corresponding loop-shaped support.

The artificial prosthetic valve may be arranged on one of the loop-shaped supports. In the case the device is intended to be inserted to the heart from the atrial side, the artificial valve is preferably arranged on the support intended to be positioned on the atrial side of annulus and vice verse.

Further, in another aspect, the invention may relate to a method for replacing a heart valve comprised of valve tissue including an annulus and a plurality of leaflets for allowing and preventing blood flow, the method comprising: inserting a device comprising an artificial valve, at least a loop-shaped support and at least one flange unit being connected to the loop-shaped support to a heart valve, positioning the loop-shaped support such that it abuts a first side of the heart valve, positioning the flange unit such that it abuts the annulus, and fixating the device by attaching the flange unit to the annulus.

The advantages provided by a device having a flange unit and an artificial valve have previously been discussed above. The inventive method for replacing a heart valve uses a corresponding device, whereby the same benefits are achieved.

The flange unit may be attached to the annulus by using suitable fixation units, e.g. sutures or clips, which allows for a quick fixation using well established means.

The flange unit may be conformed to the annulus before fixating the device. By conforming the flange to the annulos the surface to be covered by endothelia is reduced, allowing the growth to be enhanced and accelerated.

The device may be inserted to the heart valve by using a catheter, whereupon the catheter is withdrawn leaving the device.

In the method, the first side of the heart valve is preferably the atrial side.

The artificial valve may be arranged on one of said loop-shaped supports.

Further embodiments of the invention are defined in the dependent claims, wherein features for the second and subsequent aspects of the invention are as for the first aspect mutatis mutandis.

Some embodiments of the invention provide for a reduced amount of time used to repair and/or replace cardiac valves.

Some embodiments of the invention also provide for a reduced or prevented backflow of blood, e.g. by a smooth transition section may be formed between the outer periphery of the device and annulus.

Some embodiments of the invention provide for a more convenient repair, e.g. by means of a well defined surface for attachment of fixating means such as sutures or clips.

Some embodiments of the invention provide for a smooth formation and growth of endothelia.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which FIG. 1 schematically illustrates a patient with a heart shown in cross-section and a device of an embodiment of the present invention schematically illustrated as supporting the mitral valve.

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Figure 1:
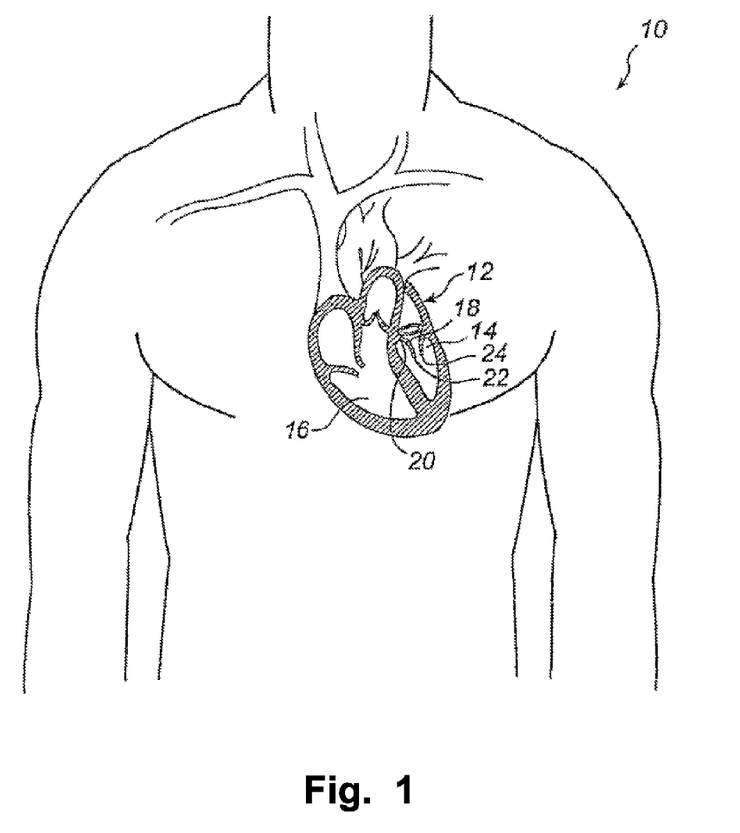
Figure 1A:
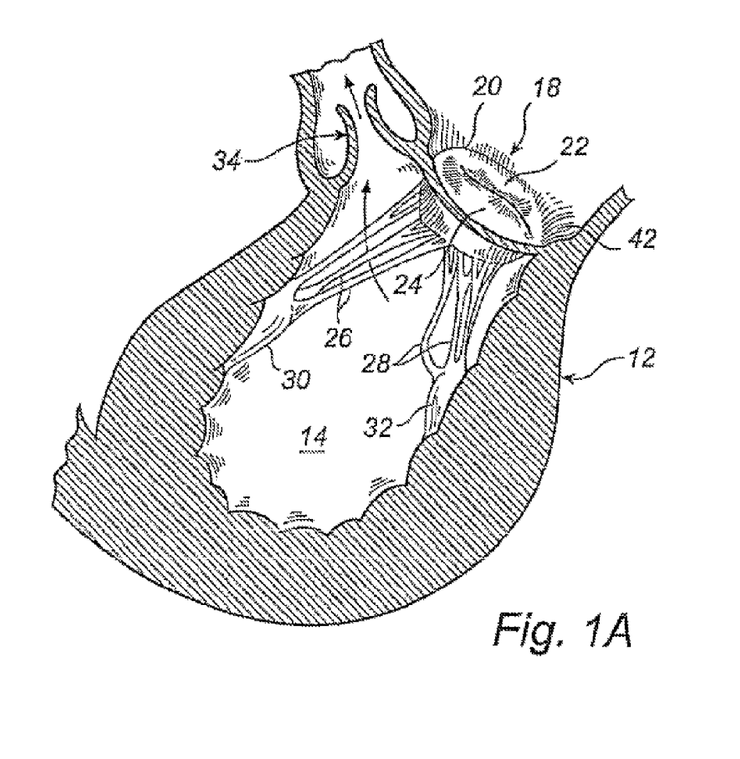
FIG. 1A is a cross-sectional view of the left ventricle showing the mitral valve in perspective.

FIG. 1 illustrates a patient 10 having a heart 12 shown in cross-section including a left ventricle 14 and a right ventricle 16. The concepts of the present invention are suitable to be applied, for example, to a mitral valve 18 which supplies blood into left ventricle 14. Mitral valve 18, as better shown in FIG. 1A, includes an annulus 20 and a pair of leaflets 22, 24 which selectively allow and prevent blood flow into left ventricle 14. It will be appreciated that the term valve tissue is used extensively throughout this disclosure in reference to the drawings. The inventive principles are equally applicable when referring to any valve tissue such as annulus tissue, leaflet tissue or other attached vessel tissue. Leaflets 22, 24 are supported for coaptation by chordae tendinae or chords 26, 28 extending upwardly from respective papillary muscles 30, 32. Blood enters left ventricle 14 through mitral valve 18 and is expelled during subsequent contraction of heart 12 through aortic valve 34. It will be appreciated that the present invention is applicable to tricuspidal heart valves as well.

Figure 2:
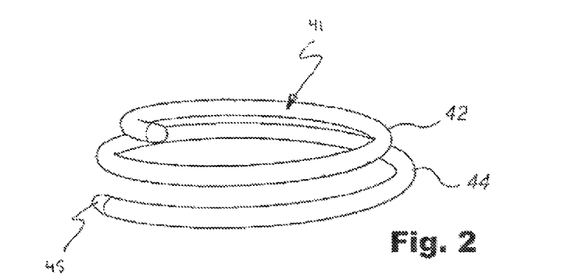
FIG. 2 is a perspective view of a body of a device according to a first embodiment of the invention.
Figure 3:
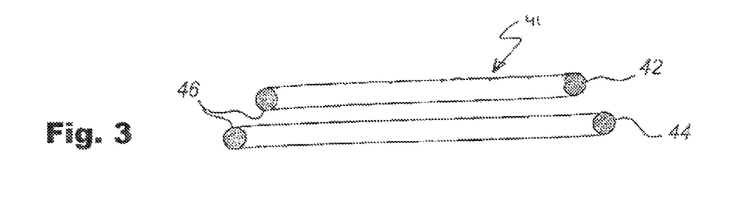
FIG. 3 is a cross-sectional view of the body in FIG. 2.

A body 41 comprised in a device 40 according to a first embodiment of the present invention is shown in FIGS. 2 and 3. The body 41 comprises a first and a second loop-shaped support 42, 44.

As used herein, the term "loop-shaped" should be construed as a curved shape that may be closed, as at least a part of a ring with e.g. a circular, elliptic, or D-shaped form or any other closed form which may fit the shape of the valve annulus. The term "loop-shaped" also includes a curved shape that is open forming an arcuate shape, such as a C-shape or U-shape, which includes an angular turn of at least 180° such that the support may abut valve tissue along a major part of the annular valve shape. The term "loop-shaped" also includes a curved shape overlapping itself to form a portion of a coil.

The term "loop-shaped" also includes three dimensional curves as mentioned in the previous paragraph.

The loop shape of at least a part of at least one of the supports 42, 44 may also in some embodiments be patient configured. The shape may be designed specifically to an anatomy of a patient. The patient specific loop shape may be virtually derived from 3D patient data, e.g. acquired by image modalities, such as Magnetic Resonance (MR) or Computer Tomography (CT) Imaging.

In U.S. Pat. No. 6,419,696, U.S. Pat. No. 6,730,121, U.S. Pat. No. 6,964,684, and WO 2006/091163, which are assigned to the same applicant as the present invention and incorporated by reference herein in their entirety for all purposes, devices are disclosed for repairing and replacing a heart valve in various embodiments. The devices include at least first and second support rings connected together in loop-shaped configurations to abut opposite sides of a valve annulus. A replacement valve may be secured to the loop-shaped devices.

The first support 42 may be continuous and/or integral with the second support 44 such that the supports 42, 44 assume a coiled configuration in the form of a spiral or keyring-type configuration with two loops.

The second support 44 may have an outer boundary or extent which is greater in relation to the outer boundary of the first support 42. The supports 42, 44 may in an embodiment have corresponding shapes with the second support 44 being in larger scale than the first support 42. This is advantageous in creating a pinch of the valve tissue between the first 42 and second supports 44.

An end 45 of the second support 44, which will lead the coil during insertion of the device at the valve, may in an embodiment have a greater pitch than the rest of the coil. This implies that the leading end 45 of the coil during rotation into position in the valve will project from immediate contact with the valve tissue and, therefore, the risk that the coil is caught by the chords is diminished.

The body 41 is shown in cross-section in FIG. 3. The body 41 has in an embodiment at least partly a round cross-sectional shape. In other embodiments, the cross section of the body 41 may be substantially flat, oval, flattened and/or have flattened edges.

In embodiments, the opposed surfaces 46 thus provide a pinch to trap valve tissue there between. A round cross-section is also advantageous in creating a pinch of the valve tissue which will not harm the leaflets in their movement during normal heart action.

The second loop-shaped support 44 is slightly displaced radially with respect to the first loop-shaped support 42. This implies that the first and second loop-shaped supports 42, 44 are not arranged directly on top of each other in some embodiments. The pinch between the first 42 and second supports 44 is therefore not sharply defined in a radial direction of the valve. This implies that a pinching force between the supports is not focused to a specific radial position of the valve. As a result, the pinching force does not affect the movement of the leaflets during normal heart action and there is a diminished risk of rupture in the leaflets at the pinch.

The supports may in some embodiments be interrelated in such manner that the outer boundary of the first support 42 has a diameter corresponding to a line through the centre of the second support 44. Thus, the supports 42, 44 may overlap somewhat such that tissue is not allowed to move through the pinch and the shape of the valve is maintained advantageously.

Further, the cross-section of the supports 42, 44 is substantially round, which also gives a soft contact between the supports and the valve tissue to further diminish the risk of rupture in the leaflets.

The body 41 may be formed from a core of a rigid material, such as a metal, e.g., titanium, or plastic. Any suitable medical grade material(s) may be used.

The rigid material may provide a passive spring function such that the loops of the coil may be forced a small distance away from each other but will flex back towards each other when the force is released. The core of the body 41 may be coated by a softer layer, such as a textile.

The body 41 may alternatively be formed from a shape memory material. The body 41 will then assume a desired, programmed shape, when e.g. heated to a specific temperature. This allows the body 41 to be compressed or straightened of the form better suited for delivering during insertion and to assume a spiral shape when inserted at the heart valve. Also, the flange unit may be made of such a shape memory material, e.g. to provide a first, delivery shape and a second, delivered shape thereof.

Figure 4:
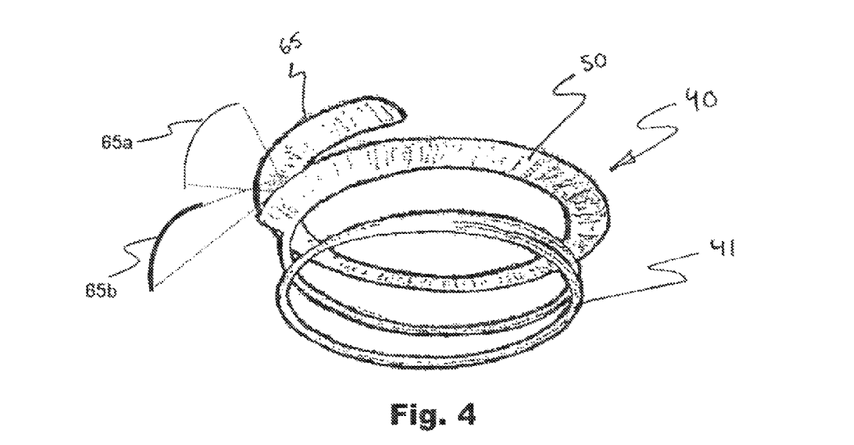
FIG. 4 is a perspective view of the first embodiment of the device comprising the body shown in FIG. 2.
Figure 5:
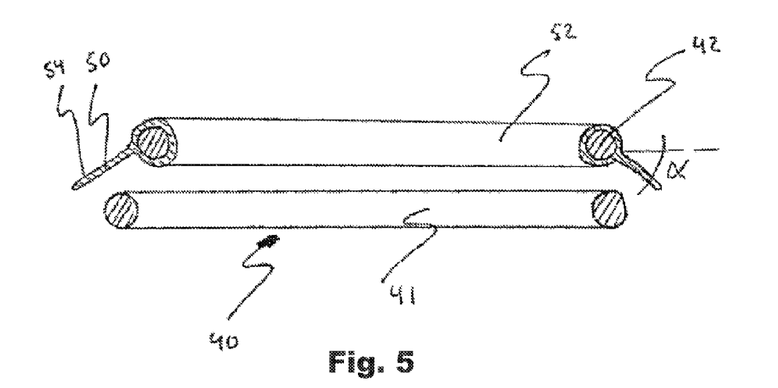
FIG. 5 is a cross-sectional view of the device in FIG. 4.

Now turning to FIGS. 4 and 5, a first embodiment of the medical device 40 is disclosed. The device 40 comprises a body 41 in accordance with that described above with reference to FIGS. 2 and 3, whereby the body 41 as such is not further discussed.

The device 40 comprises a flange unit 50 being connected to the body 41 and more precisely to the first loop-shaped support 42. The flange unit 50 has in an embodiment a continuous extension along the periphery of the first loop-shaped support 42.

Figure 16A:
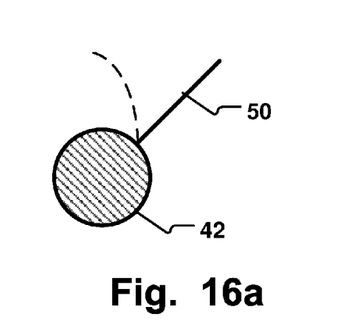
FIG. 16a, 16b are cross sectional views of embodiments involving a shape change.

In some embodiments, the flange unit 50 may be integral with at least a portion of the body 41, as e.g. shown in FIG. 16a.

In some embodiments the flange unit 50 is made of a tube shaped flexible material 52 being passed onto the first loop-shaped support 42, whereby a loose substantially co-axial connection between the loop-shaped support and the flange unit is achieved. The connection may also be fixed or rigid. The flexible material may by way of example be a fabric or woven structure made of Polyethylene (PE) or polytetrafluoroethylene (PTFE). A fabric has the advantage that it presents a rough, holed or porous surface enhancing growth of and overgrowth of endothelia. Further, a fabric is easily penetrated by sutures or clips. In addition, the flexible material admits the flange unit 50 to be conformed to the annulus.

The flange unit 50 does in the disclosed embodiment form a flange surface 54 extending downwards out from the body. More precisely the flange unit 50 forms in some embodiments and angle α to a horizontal, diametric plane formed by the first loop-shaped support. The angle α is approximately between 30-60°, such as 40-50° to the diametric plane. Such angle improves the visibility during insertion of the device. In some embodiments, improved visibility may be provided during insertion of the device, whereupon the flange unit 50 changes shape to a position facilitating fixation thereof to surrounding tissue. Thus, medical procedures for heart valve repair and/or replacement may be speeded up considerably.

In a practical embodiment the flange surface 54 has a width in the range of approximately 2-4 mm such as 2.5-3.5 mm. The width of the flange radially outwards allows an indication for the surgeon of the area in which sutures or clips should be positioned when fixating the device to the annulus. This is further discussed below with reference to FIG. 13.

Initially, before inserted into the heart valve, the flange surface 54 extends downwardly. When positioned in the atrial side of the heart valve, the device will be arranged abutting the annulus whereby the flange unit will be conformed to the annulus, changing its angle from extending downwardly to extending upwardly. This ability to conform is a combination of the flexibility of the (fabric) material and the width of the flange means.

On its outer periphery, the flange unit 50 may comprise a reinforcing element 65, which is schematically illustrated in FIG. 4. Such reinforcing element may by way of example have the form of a thread 65a or a bead 65b.

Figure 6:
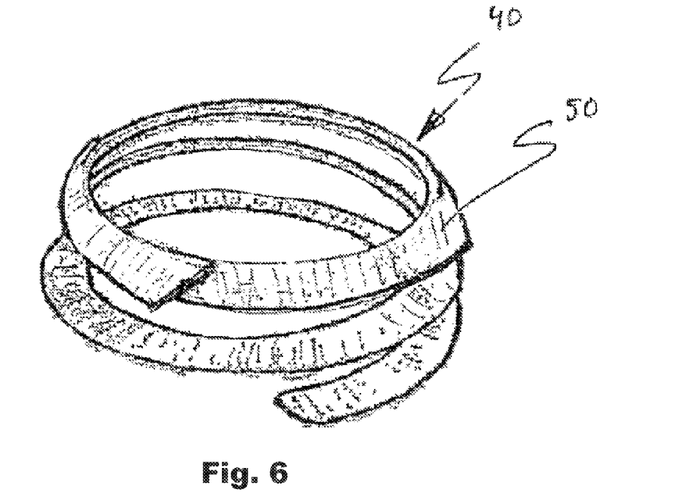
FIG. 6 is a perspective view of a second embodiment of the device.

Now turning to FIG. 6, a second embodiment of the device 40 is disclosed. The device differs from that disclosed in FIGS. 4 and 5 in that the flange unit 50 extends from the first loop-shaped support 42 to the second loop-shaped support 44. The flange unit 50 may be formed in one piece or be separated into a first and a second piece, wherein the first piece is connected to the first loop-shaped support and the second piece is connected to the second loop-shaped support. The connection may be a rigid connection or a loose connection. The latter may be achieved by the flange unit being passed onto the loop-shaped support(s).

The flange unit may be continuous or intermittent along its extension.

The second embodiment is suitable no matter if the device is to be used for repairing or replacing a valve.

Figure 7:
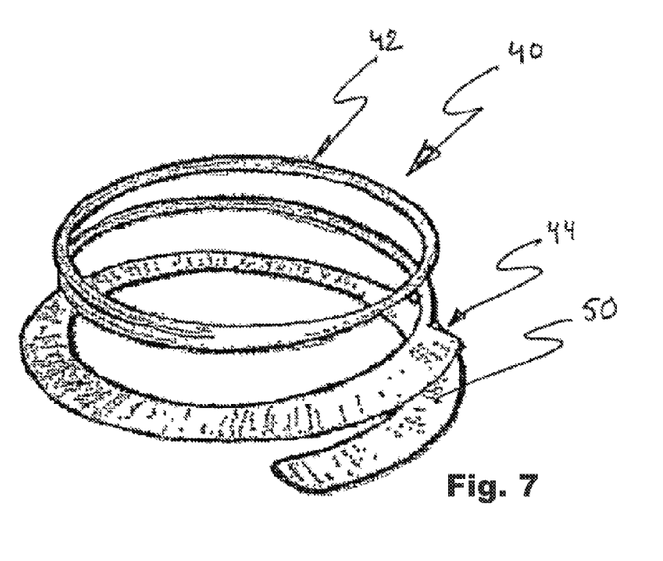
FIG. 7 is a perspective view of a third embodiment of the device.

Now turning to FIG. 7, a third embodiment of the device 40 is disclosed. The device 40 differs from that disclosed in FIGS. 4 and 5 in that the flange unit 50 extends along the second loop-shaped support 44. When positioned in the heart valve, the second loop-shaped support 44 is intended to abut the ventricle side of the heart valve, whereas the first loop-shaped support 42 is intended to abut the atrial side. The flange unit 50 may be continuous or intermittent along its extension. The third embodiment may be suitable when used in valve replacement. An artificial, i.e. prosthetic valve may be carried by either the body or the flange means.

Figure 8:
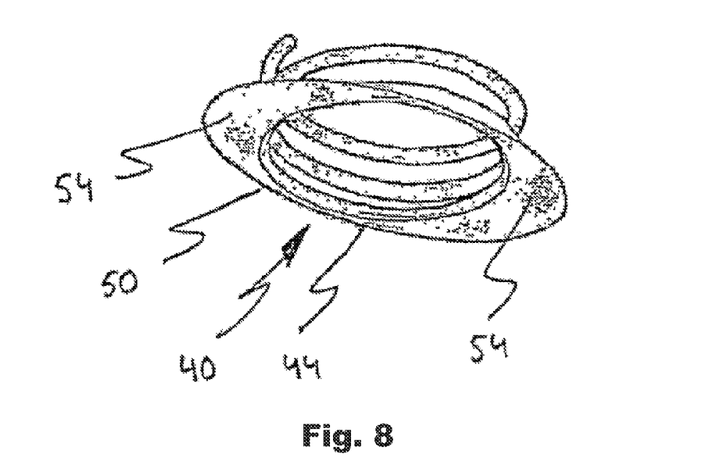
FIG. 8 is a perspective view of a fourth embodiment of the device.

Now turning to FIG. 8, a fourth embodiment of the device 40 is disclosed. The device 40 differs from that disclosed in FIGS. 4 and 5 in that the flange unit 50 extends along the second loop-shaped support 44 and forms two flange surfaces 54, both being connected to the second loop-shaped support 44. The flange surfaces 54 are so arranged on the loop-shaped support 44 that they overlap the commissures when the device is arranged in the heart valve abutting the annulus. Thereby the two flange surfaces form a sealing preventing possible leakage of blood from the ventricle side to the atrial side.

In the above discussed embodiments of the device, the flange unit has been disclosed as being either continuous or intermittent along its extension. The flange unit may further have a non-uniform width varying along its extension. By way of example the width may be larger in a region corresponding to a position overlapping the commissure when the device is arranged in the heart valve abutting the annulus.

Figure 9A:
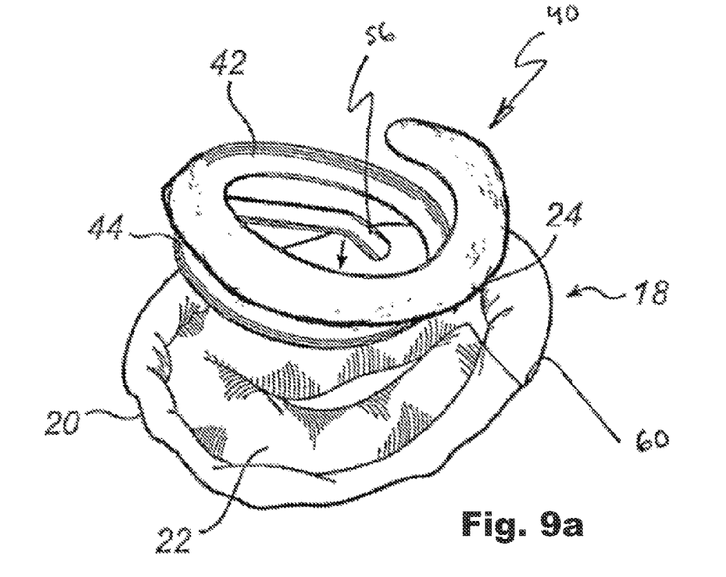
FIG. 9a, 9b are perspective views that illustrate insertion of an embodiment of the device.
Figure 9B:
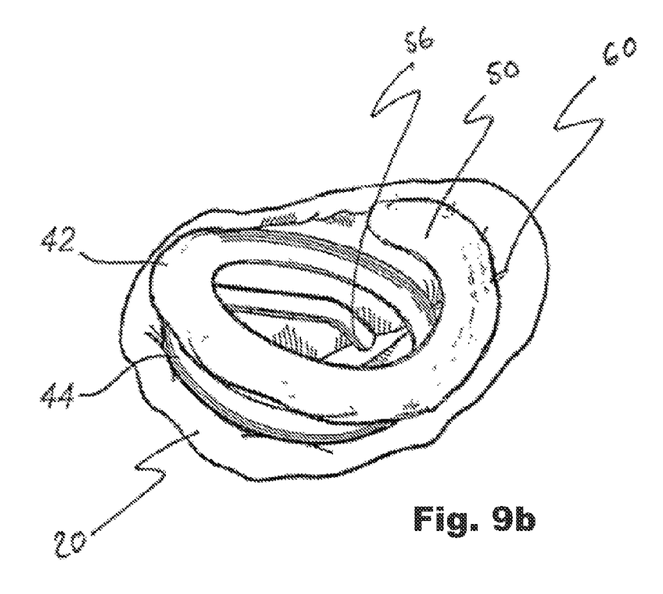
Figure 10:
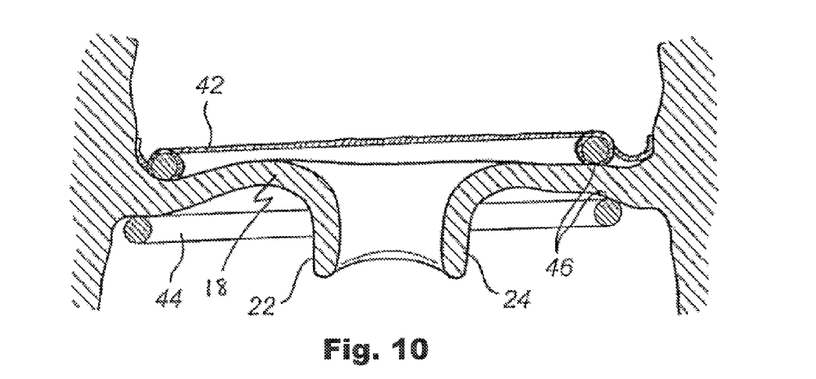
FIG. 10 is a cross-sectional view showing an embodiment of the device inserted in a heart valve.
Figure 11:
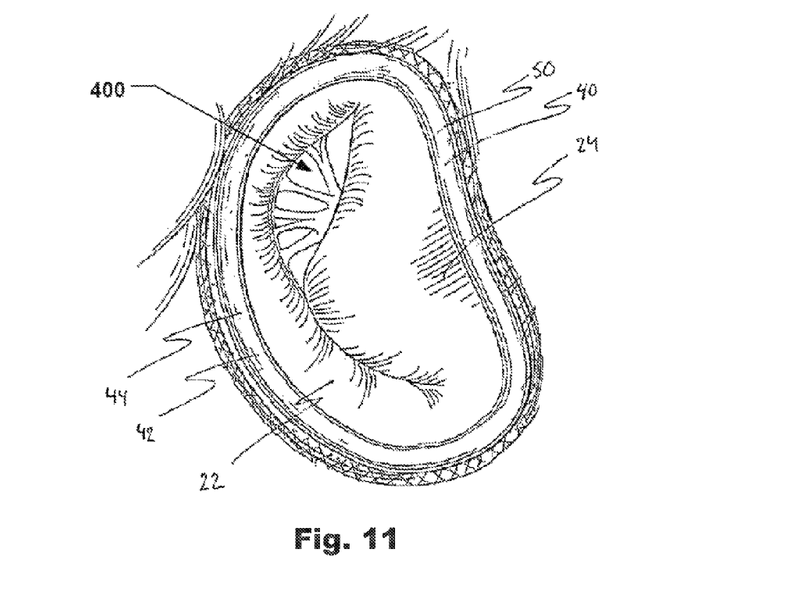
FIGS. 11 and 12 are schematic illustrations that show a heart valve before and after remodeling by using the device.

Referring now to FIGS. 9-11, a method for repairing a heart valve by means of the device according to the first embodiment will be described.

First, access to the heart valve is achieved by conventional techniques, including arresting the heart and opening the chest. Alternatively, an intraluminal catheter based delivery technique may be applied. In FIG. 9a, the device 40 is shown when being inserted to the mitral valve 18 from the atrial side. The device 40 is being carried on a carrier or tool (not shown), which is connected to a stem for remote control of the positioning of the carrier. An end 56 of the second loop-shaped support 44 is brought to the opening of the mitral valve 18 at a commissure 60 between the leaflets 22, 24, as shown in FIG. 9b. The end 56 is led through the opening and the carrier is turned 360 degrees. Thus, the second support 44 will be rotated into place on one side of the valve 18, whereas the first support 42 and the flange unit is placed on the opposite side of the valve 18. During this rotational movement the flange unit 50 is deflected from its original direction forming an angle of 30-60° downwards from the diametric plane formed by the support 42 to a direction extending in an angle upwards from the diametric plane corresponding to the wall formed by the annulus 20. The deflection allowed by the flexibility of the flange unit 50 results in a close abutment between the flange unit 50 and the atrial side of the annulus 20. If necessary, the flange unit 50 may be additionally conformed to the annulus 20. In this way, the device 40 is arranged in engagement with the valve 18, as shown in FIG. 10.

Figure 12:
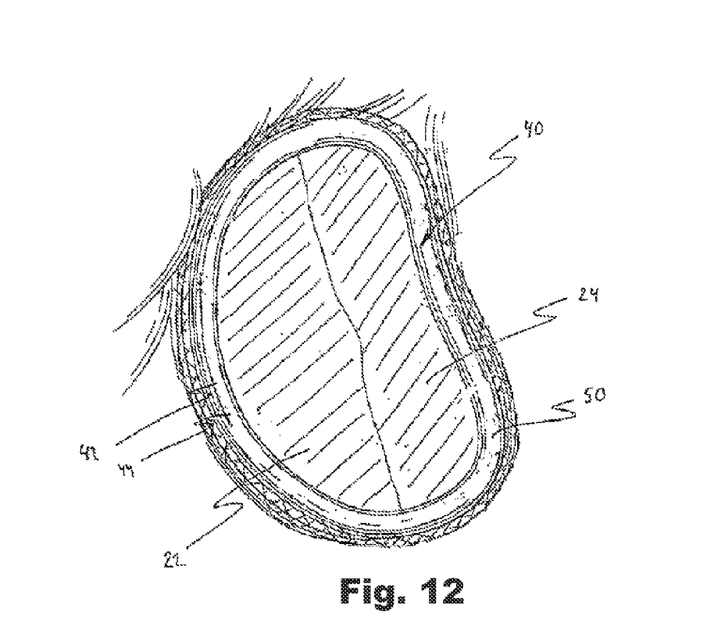

Further, the supports 42, 44 are placed on opposite sides of the valve 18 pinching valve tissue between them to maintain a shape of the valve 18. The leaflets 22, 24 may now be drawn towards each other through the pinch of the support rings 42, 44 so as to remodel the shape of the valve 18. The leaflets may be drawn through the pinch by means of a forceps instrument. The supports 42, 44 may flex away from each other to allow drawing leaflets 22, 24 through the pinch and towards each other for preventing the leaflets 22, 24 to slip back. The valve annulus 20 may in this way be remodeled and the new shape is maintained by the supports 42, 44, see FIGS. 11 and 12 showing before and after remodeling. In FIG. 11 a defective closure region 400 of the valve leaflets 22, 24 is shown. The supports 42, 44 may have roughened, opposed surfaces 46 to better keep the leaflets 22, 24 from slipping through the pinch and to hold the valve annulus 20 in its reshaped form.

Figure 13:
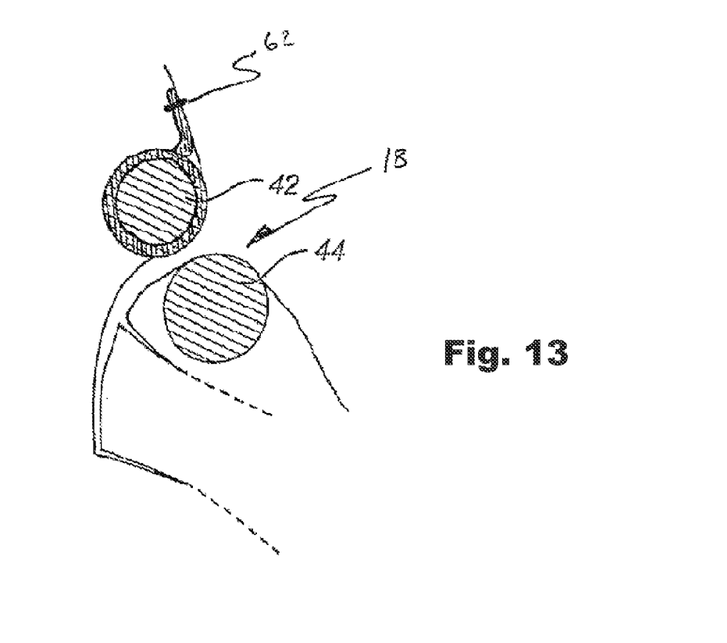
FIG. 13 is a cross sectional view that shows the device fixed to the annulus.

The device 40 may now be secured to the valve 18 for strengthening the fixation of the relative position between the supports 42, 44 and the valve tissue, see FIG. 13. The fixation may be made by clips or sutures 62 which are arranged through the flange unit 50 and its circumferential flange surface 54. By the latter being made of fabric it is easily penetrated. The clips or sutures 62 are preferably oriented and positioned in the circumferential direction of the flange unit 50. The number of fixation points is arbitrary for the provision of a durable fixation.

The flange unit 50 provides in some embodiments a better seat and prevents sliding of the device 40. Thus, the device 40 is positioned more stable in the procedure, which is advantageous, especially for long-term performance of the device after insertion.

As illustrated in FIG. 10, the second support 44 is slightly displaced radially with respect to the first support 42. This implies that the first and second supports 42, 44 are not arranged directly on top of each other. The pinch between the first and second supports is therefore not sharply defined in a radial direction of the valve. This implies that a pinching force between the supports is not focused to a specific radial position of the valve. As a result, the pinching force does not affect the movement of the leaflets during normal heart action and there is a diminished risk of rupture in the leaflets at the pinch. The supports are interrelated in such manner that the outer boundary of the first support 42 has a diameter corresponding to a line through the centre of the second support 44. Thus, the supports 42, 44 overlap somewhat such that tissue is not allowed to move through the pinch and the shape of the valve is maintained. Further, the cross-section of the supports 42, 44 is round, which also gives a soft contact between the supports and the valve tissue to further diminish the risk of rupture in the leaflets.

The method described above is applicable no matter the shape, position or extension of the flange means. Further, the method is applicable no matter if the device is inserted from the atrial side or the ventricle side.

A device having a flange unit on the first, upper loop-shaped support is suitable when the device is to be positioned on the atrial side, providing a fixation surface to the atrial side of the annulus. Such device is also suitable when carrying an artificial valve. Further, a device having a flange unit on the second loop-shaped support is suitable when the second loop-shaped support is to be positioned on the ventricle side of the heart valve.

A device having a flange unit extending from the first to the second loop-shaped support is suitable no matter if the device is positioned on the atrial side or the ventricle side of the heart valve.

Figure 14A:
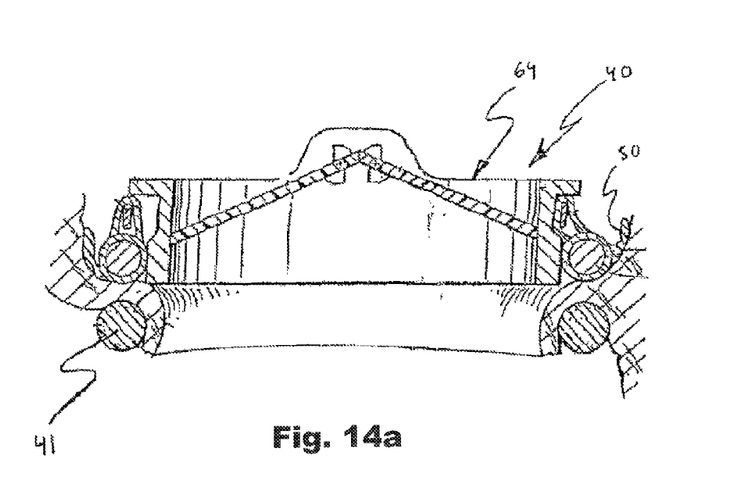
FIG. 14a is a cross sectional view that shows a first embodiment of the device comprising an artificial prosthetic heart valve.
Figure 14B:
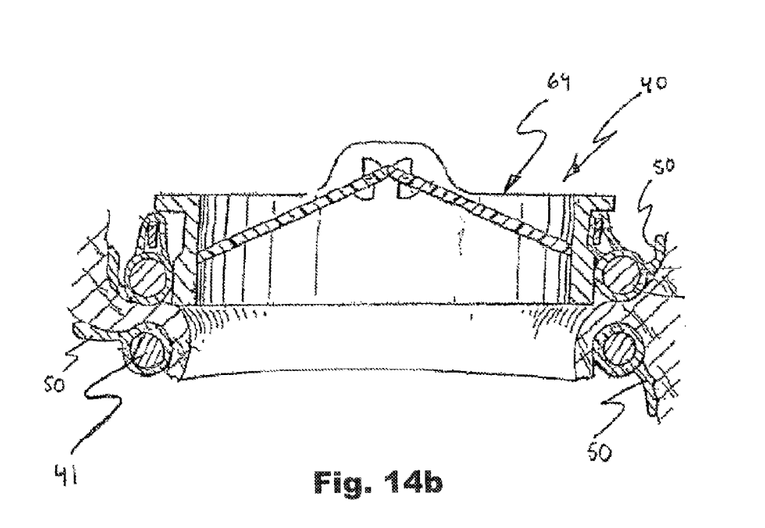
FIG. 14b is a cross sectional view that shows a second embodiment of the device comprising an artificial valve.

With reference to FIG. 14*a* and FIG. 14*b*, it is to be understood that the device may be used for replacement of heart valves as well. For that purpose the device 40 comprises in addition to a body 41 and a flange unit 50 an artificial valve 64. The flange unit 50 may be carried by the first loop shaped support 42 as is shown in FIG. 14*a*. Alternatively, as is shown in FIG. 14*b*, the flange unit 50 may extend from the first 42 to the second 44 support. Although not shown, it is to be understood that each support 42, 44 may carry its own flange unit 50, or that the flange unit may be carried by the second support 44 only.

The method of inserting, positioning and fixation of the device is generally the same as that used when repairing a heart valve, whereby the method as such is not further discussed.

It should be emphasized that the preferred embodiments described herein are in no way limiting and that many alternative embodiments are possible within the scope of protection defined by the appended claims.

Figure 15:
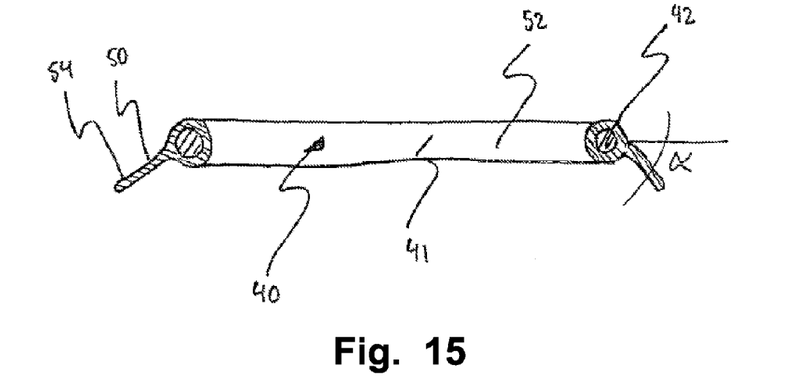
FIG. 15 is a cross-sectional view of an alternative device having one loop-shaped support carrying the flange unit.

By way of example, the device 40 and its body 41 has been disclosed as having a first 42 and a second 44 loop-shaped support. The device 40 is applicable with only one loop-shaped support carrying the flange unit 50. One such embodiment is disclosed in FIG. 15.

Further, the access to the heart valve may be achieved endoscopically, or transluminally, catheter based. In such case, the device 40 needs to be inserted through a narrow tube (endoscope or catheter). This implies that the device 40 will need to be compressed during insertion in order to pass through the endoscope or catheter. The device 40 needs to assume its proper shape after having been passed through the endoscope. Therefore, using an endoscopic or catheter based approach, the body may advantageously be formed from a shape memory material. This allows the device 40 to be compressed and also to have a stable shape when being applied to the heart valve. In the alternative, where the access to the heart valve may be achieved through a catheter, which is passed through the vascular system to the heart. In this case, the supports may be formed from a shape-memory material, which during insertion extends along the catheter in a flexible state and, when pushed out of the catheter at the heart valve, assumes a pre-stressed coil-shape in order to abut the heart valve on opposite sides.

The first and second loop-shaped supports may be connected to each other by means of a connecting part so as to form a coil-shape. The coil-shape of the device is advantageous during insertion, since the device may then be rotated into position, as described above. However, the connecting part is detachable from at least one of the supports. Thus, when the device has been inserted, the connecting part may be detached and removed from the opening of the valve.

The loop-shaped support(s) and the flange unit may be provided as separate parts.

Further, it is to be understood that the flange means, or at least a wing part thereof, may form an arbitrary angle to its corresponding loop-shaped support.

Figure 16B:
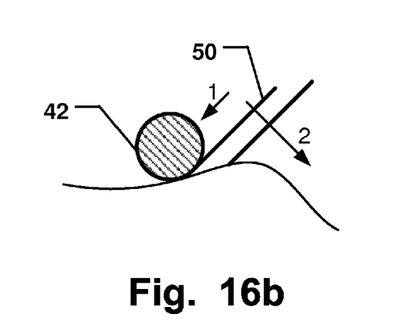

FIG. 16*a*, 16*b* are cross sectional views of embodiments involving a shape change.

In FIG. 16*a* the change of shape of a flange unit 50 is illustrated, e.g. for being out of a line of sight for a surgeon during insertion (dotted line) and, when in contact with body tissue, turning to a second shape (continuous line) for attaching to the tissue.

In FIG. 16*a* the change of shape of a flange unit 50 is illustrated in two steps or directions. Firstly the flange unit may shrink in a first direction, in order to eliminate any wrinkles or folds therein. Subsequently or concurrently, the flange unit 50 may change shape in a second direction, e.g. as described with reference to FIG. 16*a*.

Figure 17:
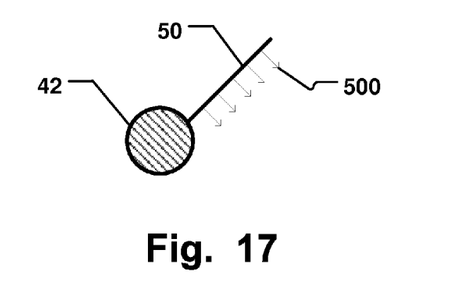
FIG. 17 is a cross sectional view schematically illustrating a flange unit having barb elements for affixing to tissue.

FIG. 17 is a cross sectional view schematically illustrating a flange unit 50 having barb elements 500 for affixing the device 40 to tissue. The flange unit 50 may thus be a carrier for fixation elements. The flange unit 50 may thus be inserted into the body more effectively.

In some embodiments, different materials may be used for parts of the device 40. For instance, the inner rings 42, 44 may be made of a stiffer more stable than a more flexible outer part, e.g. the flange unit 50.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention as limited by the appended patent claims.

What is claimed is:

1. A method for repairing a heart valve, said heart valve being comprised of valve tissue including an annulus and a plurality of leaflets for allowing and preventing blood flow, said method comprising:
    delivering a medical device comprising a first loop-shaped support and a first flange unit extending radially from the said first loop-shaped support to the heart valve,
    positioning said first loop-shaped support such that it abuts a first side of the heart valve,
    positioning said first flange unit such that it abuts said annulus,
    sealing said first flange unit against said annulus with a sealing surface of said first flange unit,
    fixating said device by attaching said first flange unit to said annulus
    wherein:
    said first flange unit extends radially downward at an angle α of between 30° and 60° to a diametric plane of said first loop-shaped support before said positioning to abut the first side of the heart valve and
    positioning said first flange unit such that it abuts said annulus comprises conforming said first flange unit to said annulus and thereby changing the shape of said first flange unit to extend upwardly from said annulus.

2. The method according to claim 1, wherein said first flange unit extends radially inwards and said method comprises supporting said leaflets with said flange unit.

3. The method according to claim 1, wherein an outer periphery of said first flange unit comprises a reinforcing element and said method comprises conforming the flange unit to the annulus before fixating said device by placing staples and/or sutures in an area of said flange comprising said reinforcing element.

4. The method according to claim 1, wherein said delivering of the device to the heart valve is performed using a catheter.

5. The method according to claim 1, wherein said first side of the heart valve is the atrial side.

6. The method according to claim 4, wherein said first loop-shaped support is made of a memory shape material and said method further comprises compressing said device into a delivery shape before delivery to the heart valve and changing the device to a delivered shape after delivery.

7. The method according to claim 1, wherein said medical device further comprises a second loop-shaped support and the method further comprises:
    positioning said second loop-shaped support such that it abuts a second side of the heart valve opposite to said first side and
    trapping a portion of the valve tissue between the first and second loop-shaped supports.

8. A method for replacing a heart valve, said method comprising:
    delivering a medical device to the heart valve, said device comprising an artificial valve, a first loop-shaped support and a flange unit extending radially from the loop-shaped support,
    positioning the loop-shaped support such that the medical device abuts only a ventricular side or an atrial side of the heart valve,
    positioning the flange unit such that it abuts the annulus,
    sealing said flange unit against said annulus with a sealing surface of said flange unit, and
    fixating the device by attaching the flange unit to the annulus
    wherein:
    said flange unit extends radially downward at an angle α of between 30° and 60° to a diametric plane of said first loop-shaped support before said positioning to abut the first side of the heart valve and
    positioning said flange unit such that it abuts said annulus comprises conforming said first flange unit to said annulus and thereby changing the shape of said first flange unit to extend upwardly from said annulus.

9. A method of treating a heart valve problem comprising:
    providing an implant having a coil-shaped support frame and a flange extending radially from at least a first portion of said coil-shaped support frame;
    abutting said first portion of said coil-shaped support frame against a first side of said heart valve;
    positioning said flange against a first side of an annulus of said heart valve;
    sealing said flange against said annulus;
    abutting a second portion of said coil-shaped support frame against a second side of said heart valve, opposite said first side, and thereby trapping valve tissue between said first and second portions of said coil-shaped support frame; and
    attaching said flange to said annulus;
    wherein said flange extends radially from at least a portion of said second portion of said coil-shaped support frame and said method further comprises:
    positioning said flange against said second side of said annulus;
    sealing the flange against said annulus on said second side of said heart valve; and
    attaching the flange to said annulus on said second side of said heart valve.

10. The method according to claim 8, and further comprising attaching the artificial valve to the medical device before delivering the medical device to the heart valve.

11. The method according to claim 9, wherein an outer periphery of said flange comprises a reinforcing element and said attaching said flange to said annulus comprises placing staples and/or sutures in an area of said flange comprising said reinforcing element.

12. The method according to claim 9, wherein said flange extends radially outward from said first portion of said coil-shaped support frame.

13. The method according to claim 9, wherein said flange extends radially inward from said first portion of said coil-shaped support frame.

14. The method according to claim 9, and further comprises inserting one of said first and second portions of the coil-shaped support through a commissure to extend along one side of the valve.

15. The method according to claim 9, wherein said trapping valve tissue keeps the device in a correct position during said fixating of said device.

* * * * *